United States Patent [19]

Matsumoto et al.

[11] Patent Number: 5,451,689
[45] Date of Patent: Sep. 19, 1995

[54] METHOD OF PREPARING EPOXIDE

[75] Inventors: Katsuya Matsumoto; Takashi Ebata; Koshi Koseki; Koji Okano; Hiroshi Kawakami; Hajime Matsushita, all of Yokohama, Japan

[73] Assignee: Japan Tobacco, Inc., Tokyo, Japan

[21] Appl. No.: 170,191

[22] PCT Filed: May 18, 1993

[86] PCT No.: PCT/JP93/00648
  § 371 Date: Dec. 30, 1993
  § 102(e) Date: Dec. 30, 1993

[87] PCT Pub. No.: WO93/23387
  PCT Pub. Date: Nov. 25, 1993

[30] Foreign Application Priority Data

May 20, 1992 [JP] Japan .................. 4-151138
  May 20, 1992 [JP] Japan .................. 4-151139

[51] Int. Cl.$^6$ .................. C07D 407/14; C07D 407/02
[52] U.S. Cl. .................. 549/386; 549/520; 549/518; 549/299
[58] Field of Search .............. 549/386, 520, 518, 534, 549/299

[56] References Cited

FOREIGN PATENT DOCUMENTS 0581215 2/1994 European Pat. Off. .

OTHER PUBLICATIONS

Nathu, Narendra K. et al., The Chemistry of Lauren-1-ene. II* Remote Functionalization Reactions of the Laurenan-2-ols and the 1βH-Laurenan-2-ols, Aust. J. Chem., 1980, vol. 33, pp. 1589–602.

(List continued on next page.)

Primary Examiner—Nicky Chan
Attorney, Agent, or Firm—Birch, Stewart, Kolasch & Birch

[57] ABSTRACT

There is provided a method of preparing an epoxide (1a) or (1b) shown below:

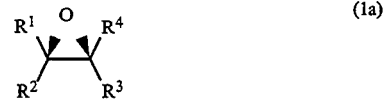

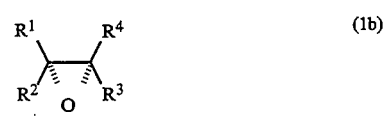

where $R^1$, $R^2$, $R^3$, and $R^4$ represent a hydrogen atom, an alkyl group, an alkenyl group, an aryl group, an alkoxy group, an aryloxy group, an acyl group, an alkyloxycarbonyl group, an aryloxycarbonyl group, allalkyl group, a silyl group, and a silyloxy group; the groups may be bonded with each other to form rings in the case where these groups can be bivalent; these groups may be the same or different, may have substituting groups, or may be branched; and each form (isomer) has a structure in which one side of the plane constituted by double bonds, $R^1$, $R^2$, $R^3$ and $R^4$, is more seterically hindered in comparison with the other side;

characterized in that:

an olefin represented by the formula (2) below, is reacted with iodine in the presence of compound generating acyloxy ion,

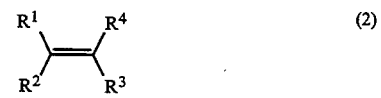

where $R^1$, $R^2$, $R^3$ and $R^4$ are the same as defined above;

and then the reaction mixture is treated in the presence of a base, thereby forming an oxirane ring stereoselectively on the more sterically hindered side of the olefin.

14 Claims, 2 Drawing Sheets

OTHER PUBLICATIONS

Rehnberg, Nicola et al., Chiral Aldehydes by Ring Contraction of Pento-and Hexopyranoside Epoxides, *J. Org. Chem.*, Feb. 23, 1990, vol. 55, pp. 5467–5476.

Georges, Michael et al., Stereo-and Regiocontrolled Synthesis of Methyl N-Acetyl-α-D-sibirosaminide, *J. Am. Chem. Soc.*, 1982, vol. 104, pp. 1101–1103.

Chemical Abstracts, vol. 120, No. 3, 17, Jan. 1994, Abstract No. 31041q, Matsumoto, Katsuya et al., "A novel synthesis of 4-deoxy-D-lyxo-hexose (4-deoxy-D-mannose) . . . ".

"A Synthesis of Methyl 4,6-Dideoxy-3-C-methyl-4-(-N-Methylacetamido)-α-D-Altropyranoside, the 3–Epimer of (Methyl N-Acetylsibirosaminide)" to M. Georges et al. Carbohydrate Research, 130, 115–124 (1984).

"D-Mannosan<1,5>β<1,6> or Levomannosan" to A. E. Knauf et al., J. American Chemical Soc., 63, 1447 (1941).

"An Anhydro Derivative of D-Mannosan<1,5->β<1.6>" to Raymond M. Hann et al., J. Am. Chem. Soc., 64, 925 (1942).

"Synthesis of 1,6:3,4-Dianhydro-β-D-Talopyranose from Levoglucosenone: Epoxidaton of Olefin via trans-Iodacetoxylation" to K. Matsumoto et al., Heterocycles, 34, 10, 1935–1947 (1992).

Woodward et al., JACS, 80, 209 (1958).

METHOD OF PREPARING EPOXIDE

TECHNICAL FIELD

The present invention relates to a method of preparing an epoxide (1a) or (1b) shown below:

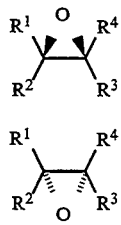

where $R^1$, $R^2$, $R^3$, and $R^4$ represent a hydrogen atom, an alkyl group, an alkenyl group, an aryl group, an alkoxy group, an aryloxy group, an acyl group, an alkyloxycarbonyl group, an aryloxycarbonyl group, aralkyl group, a silyl group, and a silyloxy group; the groups may be bonded with each other to form rings in the case where these groups can be bivalent; these groups may be the same or different, may have substituting groups, or may be branched; and each form (isomer) has a structure in which one side of the plane constituted by double bonds, $R^1$, $R^2$, $R^3$ and $R^4$, is more sterically hindered in comparison with the other side.

The present invention relates to a method of preparing an epoxide, characterized in that the oxirane ring of said epoxide is formed on the more sterically hindered side.

Further, the present invention relates to a method of preparing 1,6:3,4-dianhydro-β-D-talopyranose (1c), as shown below.

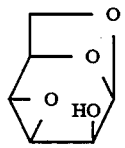

BACKGROUND ART

The compounds having oxirane ring (epoxides) are important targets in organic synthesis, since many of them themselves have biologically active. The oxirane ring in epoxide can be easily substituted by other functional groups, and therefore the epoxides are useful substances which can be employed as starting materials or intermediates for organic synthesis.

Synthesis of such epoxides is carried out through the reaction for formation of oxirane rings. The method for formation of an oxirane ring can contain, for example, the following reactions:

(i) The reaction involving oxidization of the double bond of olefin with peroxides; and
(ii) The nucleophilic substitution reaction between hydroxide groups adjacent to each other.

An example of the reaction (i) is the oxidative addition reaction (prileschajew reaction) by using peracids such as perbenzoic acid, m-chloroperbenzoic acid, and peracetic acid, as shown in equation 1 below, and another example is Scharpless oxidation in which an allyl alcohol is reacted with an appropriate oxidizing agent in the presence of metal catalyst to stereoselectively give an epoxide, as shown in equation 2 below.

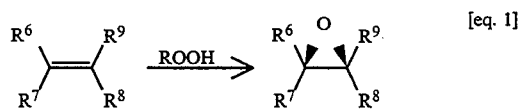

where $R^6$, $R^7$, $R^8$, and $R^9$ represent a hydrogen atom, an alkyl group, an alkenyl group, an aryl group, an alkoxy group, an aryloxy group, an acyl group, an alkyloxycarbonyl group, an aryloxycarbonyl group, an aralkyl group, a silyl group, and a silyloxy group; the groups may be bonded with each other to form rings in the case where these groups can be bivalent; and these groups may be the same or different, may contain substituting groups, or may be branched. R represents an alkyl group, an aryl group or an acyl group.

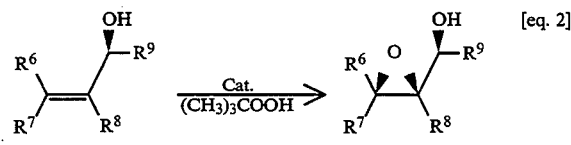

where $R^6$, $R^7$, $R^8$, and $R^9$ are defined as above, and Cat. represents a metal complex catalyst containing a metal such as vanadium, molybdenum, or titanium.

An example of the reaction (ii) is that as shown in the following equation 3. More specifically, a diol is introduced to the double bond of olefin to form a trans-isomer. Then, a leaving group is introduced to one of the two hydroxyl groups, and then the other hydroxyl group is subjected to the intramolecular nucleophilic substitution reaction, thereby forming a oxirane.

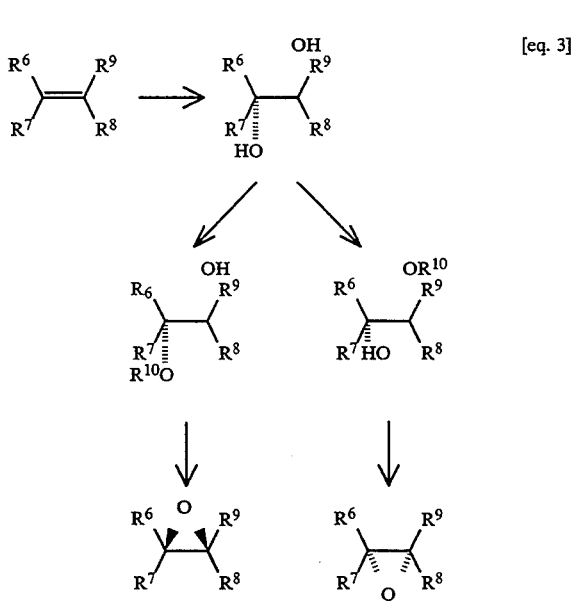

where $R^6$, $R^7$, $R^8$, and $R^9$ are the same as defined as above; and $R^{10}$ is a protecting group for a hydroxyl group, which can be released as $R^{10}O-$, for example, a acyl group.

In the synthesis of an epoxide, the stereochemistry of the oxirane ring introduced to the double bond is important. In a chain (open ring) type olefin, the conversion of the double bond of the olefin to oxirane ring can be formed an epoxide which can produce two possible diols of threo or erythro isomers after the epoxide is hydrolyzed, depending on the direction of approach of an oxidizing agent such as peracids to double bond plane. Also, in the case of a cyclic compound, two possible isomers can be obtained. These isomers can be formed depending on the direction of approach of an oxidizing agent to the ring plane.

Thus, the stereoselectivity between these isomers, and the control of the selectivity are of the great importance. Particular, it is difficult, with the conventional technique, to form an oxirane ring selectively on the more sterically hindered side of the double bond.

For example, in the reaction (i) for preparing an oxirane ring by use of peroxide, since the peroxide approaches to the less hindered side, an oxirane ring is formed on that side. Therefore, it is difficult to obtain the other isomer having an oxirane ring on the more sterically hindered side. In the case of oxidization of the double bond of a cyclic allyl alcohol, the peroxide is attracted to the hydroxyl group by the hydrogen bonding of the peroxide to the hydroxyl group, and therefore the hydroxyl group at the allyl position is not the steric hindrance. Accordingly, an oxirane ring is formed on the more sterically hindered side of the double bond. In the case of sharpless oxidation using a metal catalyst, the selectivity is higher than that of the reaction (i), and therefore one of the isomers of the epoxide, which produce the diol compound of the threo-isomer after hydrolysis, is preferentially obtained. However, in this method, if there is a substituting group which is a steric hindrance on the same side as the hydroxyl group, a peroxide or metal catalyst cannot approach to the compound from the side where the hydroxyl group is present. As a result, this method has such a problem that the selectivity is lowered, the reaction does not proceed, or the starting material is decomposed. Further, this method suffers from the defect that it can be applied only to allyl alcohol.

With the method of forming an oxirane ring through the nucleophilic substitution reaction between adjacent hydroxyl groups in the diol which are trans form as in the reaction (ii), in order to obtain an epoxide having the desired configuration, the two hydroxyl groups must be arranged at the trans-position, and therefore the two hydroxyl groups must be stereoselectively introduced to the double bond of olefin in a trans form. Further, in some cases, it is necessary to introduce a leaving group regioselectively to one of the two hydroxyl groups and the control of the regioselectivity is difficult.

As described above, with the conventional methods, it is difficult to form an oxirane ring selectively on the more sterically hindered side of the double bond of olefin.

In the meantime, as mentioned before, epoxides are important compounds in synthetic chemistry. Of the epoxides, 1,6:3,4-dianhydro-β-D-talopyranose (1c), in particular, is used as a synthetic intermediate for a sugar compound or sugar-containing compound which is focused as a useful biologically active substance in the field of fine chemicals such as medicine and pesticides, and the utility of the compound as a starting material is expected in the future.

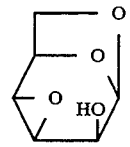

(1c)

Further, the compound (1c) is of a great importance as a synthetic intermediate of a useful antibiotics, sibiromycin (M. Georges and D. MacKay, Carbohydr. Res., 130, 115 (1984)). Furthermore, the compound (1c) can be converted into an endogenous feeding promoter substance, (2S, 4S)-2-hydroxy-4-hydroxymethyl-4-butanolide (3-DPA-lactone), through oxidization of the hydroxyl group, reductive cleavage of the oxirane ring, and Baeyer-Villigar oxidation. Furthermore, the compound can be easily converted into various types of deoxy sugars such as deoxymannose derivative and deoxyaminomannose derivative, and further into the constitutional unit of various useful saccharides, and sialic acid derivatives. However, the compound (1c) is a type containing an oxirane ring on the more sterically hindered side of the ring, and the synthesis of the compound has been difficult as mentioned above. Therefore, the development of the method of synthesizing the compound (1c) useful as a synthetic intermediate at a high efficiency is not only important in synthetic chemistry, but also significant in development of medicine and pesticides.

Conventionally, there is known a method of preparing the compound (1c), in which the compound is synthesized through a D-mannosane derivative by thermolysis of an endosperm of an ivory palm (A. E. Knauf, R. M. Hann and C. S. Hudson, J. Am. Chem. Soc., 63, 1447 (1941), R. M. Hann and C. S. Hudson, J. Am. Chem. Soc., 64, 925 (1942)).

However, the conventional method involves five steps, and the yield of the product is as low as 5%; therefore is not fully satisfactory in the number of steps, and the yield.

DISCLOSURE OF THE INVENTION

The first object of the present invention is to provide a method of preparing an epoxide at a high yield, by forming an oxirane ring stereoselectively on the more sterically hindered side of the double bond of olefin at a high yield.

The second object of the present invention is to provide a method of preparing an epoxide, characterized in that, in the case where said olefin is a cyclic compound, the oxirane ring is formed stereoselectively on the more sterically hindered side of the ring at a high yield.

The third object of the present invention is to provide a method of preparing 1,6:3,4-dianhydro-β-D-talopyranose (1c) simply and selectively from widely-available materials at a high yield.

As for the olefin expressed in the general formula (2) as a starting material, it is necessary to consider two possible isomers as shown below, olefin (2a) being more sterically hindered on this side (i.e. the upper side of the page) of the imaginary plane defined by the double bond and the substituting groups ($R^1$, $R^2$, $R^3$, and $R^4$) of the olefin, and olefin (2b) being more sterically hindered on the other side (i.e. the lower side of the page) of the imaginary plane.

upper side of page

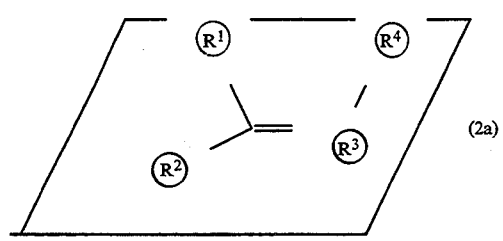

(2a)

lower side of page surface of page

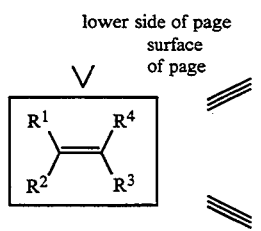

(2)

upper side of page

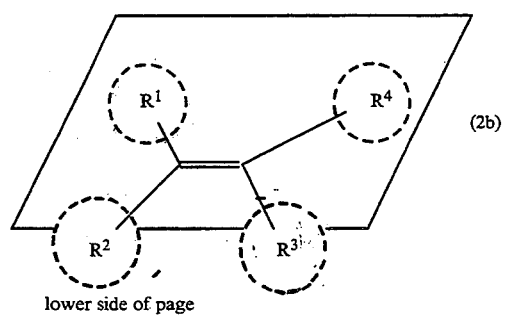

(2b)

lower side of page where $R^1$, $R^2$, $R^3$, and $R^4$ are the same as defined above.

In the present invention, the epoxide having a configuration represented by the following formula (1a) is selectively obtained from the olefin (2a), and the epoxide having a configuration represented by the following formula (1b) is selectively obtained from the olefin (2b).

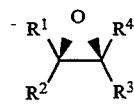

(1a)

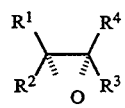

(1b)

where $R^1$, $R^2$, $R^3$, and $R^4$ are the same as defined above.

The present invention can be explained with either of the two types of olefin, since the reaction for obtaining the epoxides (1a) and (1b) from olefins (2a) and (2b) respectively proceeds by a same mechanism. Hereinafter, it is assumed that the olefin represented by general formula (2) is the olefin (2a), and the reactions and the stereochemistry of the invention will be described according to the above assumption unless otherwise noted.

For the matter of simplicity, the olefin (2a) will be represented as follows:

(2a)

where $R^1$, $R^2$, $R^3$, and $R^4$ are the same as defined before.

Again, although the explanation will be directed with the olefin (2a) for convenience, this does not mean that the present invention is limited to this type of olefin. It should be noted that the present invention can be applied to both types of olefin (2a) and (2b).

In the present invention, a "treatment with a base" is meant to be a hydrolysis by use of a base, more specifically, an alkalimetal hydroxide such as sodium hydroxide or potassium hydroxide; an alkalimetal carbonate such as sodium carbonate or potassium carbonate; a metal alkoxide such as sodium methoxide or potassium butoxide; or aqueous ammonia.

The first object of the present invention can be achieved by a method of preparing an epoxide described below.

As indicated by the following reaction formula, the olefin represented by the formula (2a) is reacted with iodine and a compound containing an acyloxy ion, and treated in the presence of a base, thereby obtaining an epoxide having an oxirane ring on the more sterically hindered side of the olefin.

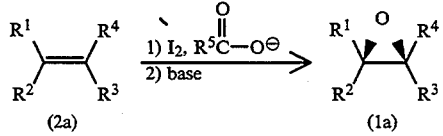

where $R^1$, $R^2$, $R^3$, and $R^4$ are the same as defined above, and $R^5$ represents an aryl group or alkyl group.

The method of preparing the above epoxide involves two steps shown below.

Step (a): Olefin (2a) is reacted with iodine to form an iodonium ion intermediate (4a) on the double bond, and the intermediate is attacked by an acyloxy ion, thereby obtaining 1,2-trans addact (3a).

Step (a)

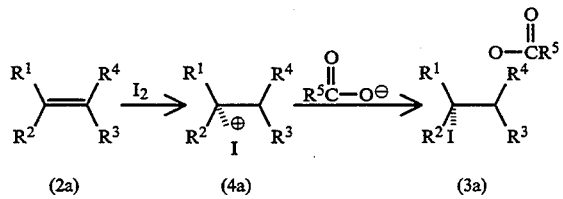

where $R^1$, $R^2$, $R^3$, $R^4$, and $R^5$ are the same as defined above.

Step (b): The 1,2-trans addact (3a) is hydrolyzed, and an oxirane ring is formed with the elimination of an iodide ion on the more sterically hindered side, thereby obtaining the target compound (1a).

Step (b)

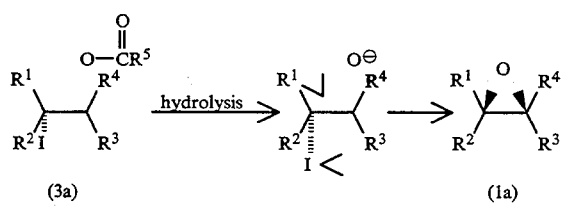

where $R^1$, $R^2$, $R^3$, $R^4$, and $R^5$ are the same as defined above.

The second object of the present invention is achieved by applying the above method of preparing the epoxide to a cyclic compound which is sterically hindered on one side of a ring.

The third object of the present invention is achieved by applying the above method of preparing the epoxide to 1,6-anhydro-3,4-dideoxy-$\beta$-D-threo-hex-3-enopyranose (2c), represented by the below formula, as a starting material.

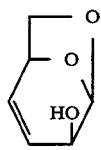

More specifically, the object can be achieved by the following steps.

Step (a'): The compound (2c) is reacted with iodine to form an iodonium ion intermediate (4c) on the double bond, and the intermediate is attacked by an acyloxy ion, thereby obtaining 1,2-trans addact (3c).

Step (a')

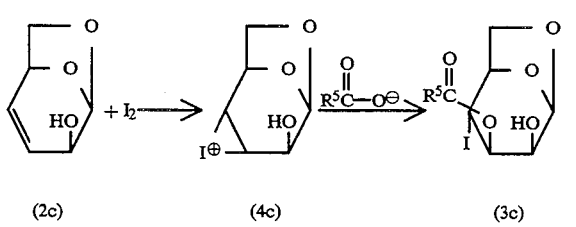

where $R^5$ is the same as defined above.

Step (b'): the 1,2-trans addact (3c) is hydrolyzed, and an oxirane ring is formed by the intramolecular nucleophilc substitution reaction with the elimination of an iodide ion, thereby obtaining the target compound (1c).

Step (b')

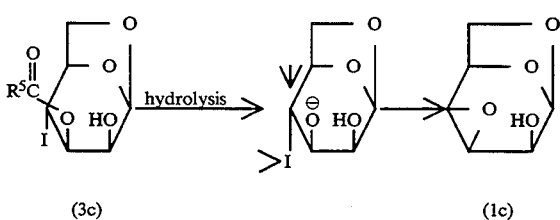

where $R^5$ is the same as defined above.

The present invention will now be described in detail.

According to the present invention, an oxirane ring can be formed on the more sterically hindered side of the double bond of olefin.

The olefin (2a) is widely available, for example, those prepared industrially or by the known method. Olefins of general types can be used without particular limitations. The substituting groups $R^1$, $R^2$, $R^3$ and $R^4$ of the olefin (2a) are not particularly limited, when these groups are hydrogen atoms, and general organic groups. Examples of the general organic groups are an alkyl group, alkenyl group, aryl group, alkoxy group, aryloxy group, acyl group, alkyloxycarbonyl group, aryloxycarbonyl group, aralkyl group, silyl group, and silyloxy group. Furthermore, in the case where the groups can be bivalent, the groups may be bonded with each other to form rings. The groups may be the same or different; each may have a substituting group; or may be branched. The compound (2a) has a more sterically hindered structure on this side (i.e. the upper side of the page) of the imaginary plane defined by the double bond and the substituting groups ($R^1$, $R^2$, $R^3$, and $R^4$) of the olefin, as compared to the other side (i.e. the lower side of the page) of the imaginary plane.

Examples of such olefin (2a) are $\alpha$-pinene, $\beta$-pinene, 2-oxabicyclo[3,3,0]oct-6-en-3-one, 1,6-anhydro-3,4-dideoxy-$\beta$-D-threo-hex-3-enopyranose, etc. However, the olefin (2a) is not limited to them.

In order to obtain the target epoxide (1c) from the olefin (2a) by the method of the present invention, the olefin (2a) is reacted with iodine in the presence of a carboxylic acid (5) or a metal carboxylate (6) represented by the formulas below, and the resultant is then treated by a base.

where $R^5$ is the same as defined above, and M represents a metal such as silver or cesium.

The reaction between the olefin (2a) and iodine carried out by stirring the olefine (2a), one or more equivalent of iodine, and one or more equivalent of the carboxylic acid (5) or the metal carboxylate (6) for the double bond of the olefin (2a) in an appropriate solution.

The solvent used in the reaction may be arbitrary, and is not restricted particularly, except for water, alcohols, or those which release water or alcohols by hydrolysis. Preferable examples of the solvent are carboxylic acid, hexane, and acetonitrile. It is most preferable that the carboxylic acid (5) itself be used as the solvent. In the case by using the carboxylic acid (5) as the solvent, any type of carboxylic acid can be used as long as the carboxylic acid is in a liquid state under the reaction condition, but acetic acid, formic acid, propionic acid, and butyric acid are preferable, with acetic acid being most preferable.

As the compound generating an acyloxy ion, the metal carboxylate (6) is preferably used, since it helps iodine to generate an iodonium ion, and the reaction is promoted. In this case, the type of the metal carboxylate (6) is not particularly limited, and examples thereof are silver carboxylate, and cesium carboxylate. More specifically, silver acetate, silver benzoate, and cesium acetate can be used. The metal carboxylate (6) is not essential to the reaction when a carboxylic acid is added to the reaction (including the case a carboxylic acid is used as the solvent), but if the metal carboxylate is added, the yield of product can be improved.

The reaction temperature and time period should be appropriately set, and in general, the temperature may be from room temperature to about 50° C., and the time may be from about 5 hours to about 10 days.

When the reaction mixture is then treated with a base, the target epoxide (1a) can be obtained.

The base used in the reaction is not particularly restricted as long as a general acyloxy group can be hydrolyzed thereby. Examples of the base are alkalimetal hydroxides such as sodium hydroxide and potassium hydroxide; alkalimetal carbonates such as sodium carbonate and potassium carbonate; metal alkoxides such as sodium methoxide and potassium butoxide; and aqueous ammonia.

The solvent used in the reaction is not particularly restricted as long as it is generally used in hydrolysis. For example, methanol, ethanol, and water are preferably used.

The reaction temperature and time period should be appropriately set, and in general, the temperature may be from about 0° C. to room temperature, and the time may be from about 5 hours to about 24 hours.

The method of preparing the epoxide, according to the present invention, will now be described in detail with regard to the following two steps (a) and (b) involved in the method.

The steps are as follows:

Step (a) is a process for obtaining 1,2-adduct (3a) by addition of iodine and an acyloxy group to the olefin (2a).

Step (a)

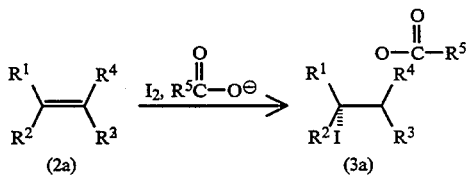

where $R^1$, $R^2$, $R^3$, $R^4$, and $R^5$ are the same as defined before.

In this step, the carboxylic acid (5) or the metal carboxylate (6) is used as a compound generating an acyloxy ion as mentioned above, and the olefin (2a) is reacted with iodine in the presence of them.

In this step, the olefin (2a) is reacted with iodine in the presence of the carboxylic acid (5) and the metal carboxylate (6) to form an iodonium ion intermediate (4a) as shown in [eq. 4]. During the reaction, iodine approaches to the olefin from the less sterically hindered side. Then, an acyloxy ion attacks the iodonium ion intermediate from the side opposite to the iodonium ion, thereby forming a 1,2-trans addact (3a). Therefore, the 1,2-trans addact (3a) prepared in this step has a configuration as shown in [eq. 4].

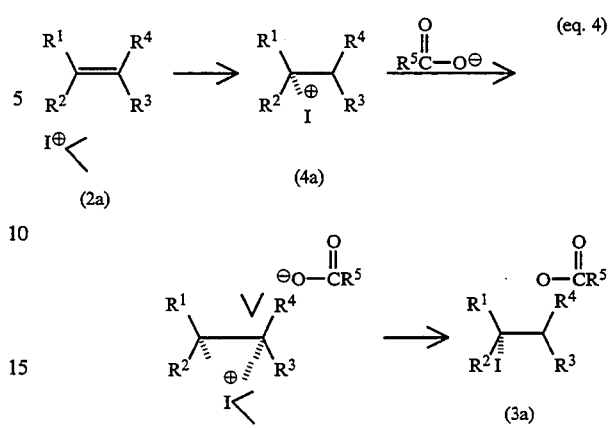

where $R^1$, $R^2$, $R^3$, $R^4$, and $R^5$ are the same as defined above.

The direction of the addition in this reaction generally depends upon the type of olefin (2a).

The solvent used in the reaction, the compound generating an acyloxy ion, the reaction temperature, and the reaction time are the same as above.

The 1,2-trans addact (3a) obtained in this step can be used in the next step without being isolated.

Step (b) is a process for treatment of the compound (3a) obtained in the step (a), with a base.

Step (b)

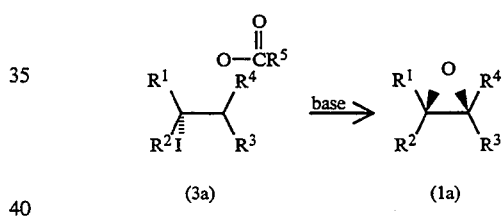

where $R^1$, $R^2$, $R^3$, $R^4$, and $R^5$ are the same as defined above.

In this step, as expressed by [eq. 5] below, the compound (3a) is treated with a base to hydrolyze the acyloxy group. An anion generated by the hydrolysis causes an intramolecular nucleophilic substitution reaction with the elimination of an iodide ion, thereby forming an oxirane ring. Thus, the oxirane ring is formed with the configuration such as the epoxide (1a) shown in [eq. 5].

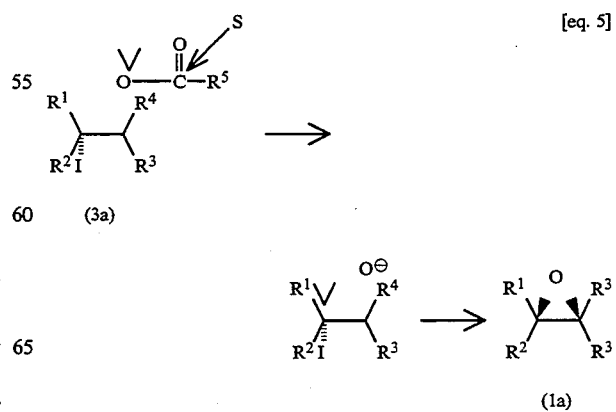

where $R^1$, $R^2$, $R^3$, $R^4$, and $R^5$ are the same as defined above, and S represents a base.

The base and the solvent used in the reaction, the reaction temperature, and the reaction time are the same as above.

With reference to FIGS. 1 and 2, the steps (a) and (b) will be described in further detail by considering stereochemistry.

An imaginary plane ABCD defined by the double bond (a=b) and the substituting groups ($R^1$, $R^2$, $R^3$, and $R^4$) is supposed, and one side of the plane is named as face α and the other as face β (FIG. 1 (I)). In this case, the substituting groups $R^1$, $R^2$, $R^3$, and $R^4$ may be not arranged flat on the plane ABCD, but projecting from either face α or face β. As a result, the molecule as a whole may be sterically hindered either on α face side or on β face side (hereinafter, the substituting groups $R^1$, $R^2$, $R^3$, and $R^4$ represent an imaginary sphere, and the β face side is more sterically hindered) (FIG. 1 (II)). In the reaction between the olefin and iodine in the step (a), an iodonium ion approaches to olefin from the less sterically hindered side, i.e. α face side, so as to form an iodonium ion intermediate (FIG. 1 (III)). Since the α face side of the intermediate is blocked by the iodonium ion, an acyloxy ion attacks from the β face side, thereby forming a 1,2-addact (FIG. 1 (IV)). Next, in the step (b), an oxygen anion produced by the hydrolysis (FIG. 2 (V)) attacks intramolecularly a carbon atom a to form an oxirane ring with the elimination of the iodide ion (FIG. 2 (VI)), thereby producing the target epoxide (FIG. 2 (VII)). In this step, since the attack of the oxygen anion takes place on the more hindered side in the molecule, the oxirane ring is formed on this side in the molecule.

As described, with the method according to the present invention, the epoxide (1a) is high-selectively obtained from the olefin (2a). As mentioned before, it is also possible in the present invention to use the other type of olefin (2b), wherein a steric hindrance around the double bond is opposite to olefin (2a) (i.e. the lower side of the page is more sterically hindered). Also in this case, the reaction proceeds by a similar mechanism to that of the above case, as expressed by [eq. 6] below. Thus, an epoxide (1b) having an oxirane ring on the more sterically hindered side (the lower side of the page) is obtained (the olefin (2b) is represented as in [eq. 6]).

[eq. 6]

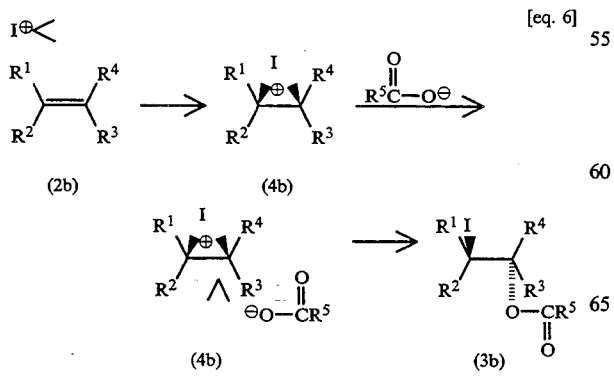

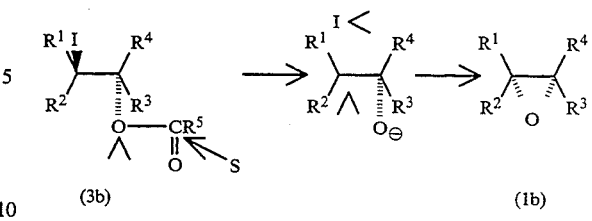

The second object of the present invention will now be described.

The second object of the invention is to provide a method of preparing an epoxide characterized in that an oxirane ring is formed stereoselectively on the more sterically hindered side of a cyclic olefin at a high yield. In order to prepare such an epoxide, the epoxide preparing method of the invention should be applied to the cyclic olefin which is more sterically hindered on one side of a ring. Of all the types of cyclic olefine which can be used in the present invention, specific examples of the compounds of a great importance particularly in terms of synthesis, and examples in which the method for preparation of an epoxide according to the invention is applied to the compounds will be set forth; however the present invention is not limited to these examples.

The epoxide preparing method can be also applied to the preparation of 1,6:3,4-dianhydro-β-D-talopyranose (1c), which is the third object of the present invention. The description of such an application will be provided later.

1) 2-oxabicyclo[3.3.0]oct-6-en-3-one (7)

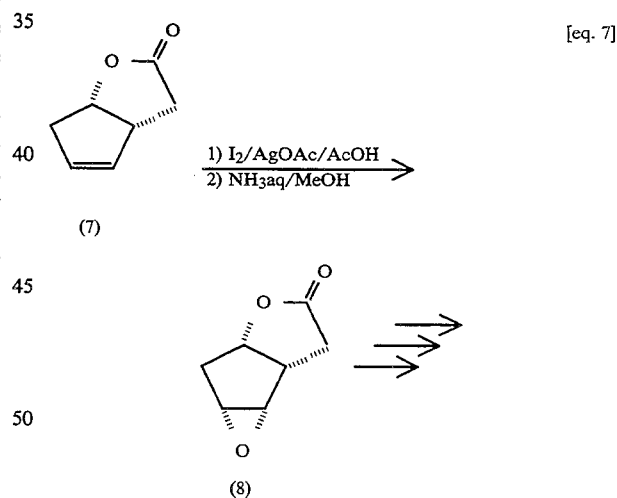

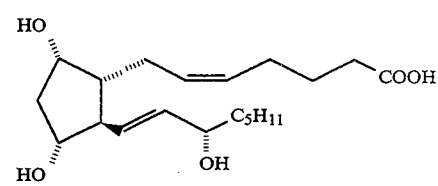

As expressed in [eq. 7], the epoxide preparing method of the invention is applied to the compound (7) which is more sterically hindered on one side of a ring to give a compound (8) having an oxirane ring on the more sterically hindered side. More specifically, one or more equivalent of iodine, and one or more equivalent of the carboxylic acid (5) or the metal carboxylate (6) for the double bond of the compound (7) are stirred in an appropriate solvent such as a carboxylic acid, hexane, or acetonitrile. Then, the reaction mixture is hydrolyzed in the presence of a base, thereby forming an oxirane ring on the more sterically hindered side of the compound (7).

The compound (8) thus obtained can be transformed into prostaglandin $F_{2\alpha}$, for example, after several steps.

2) α-pinene (9) shown in the equation below

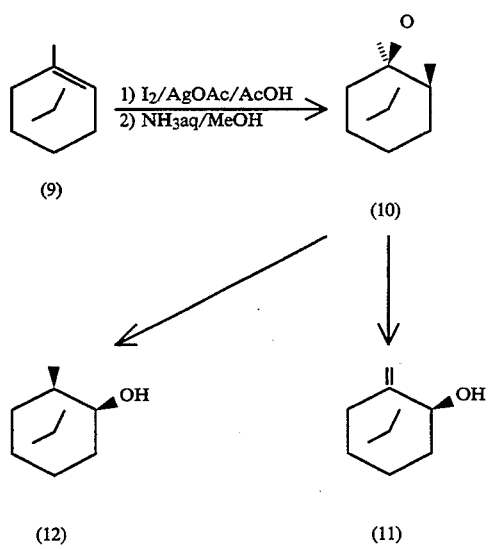

As shown in [eq. 8], by applying the epoxide preparing method of the invention to the compound (9) which is more sterically hindered on one side of a ring, there can be obtained a compound (10) having an oxirane ring on the more sterically hindered side of the compound (9). More specifically, one or more equivalent of iodine, and one weight or more equivalent of the carboxylic acid (5) or the metal carboxylate (6) for the double bond of the compound (9) are stirred in an appropriate solution such as a carboxylic acid, hexane, or acetonitrile. Then, the reaction mixture is hydrolyzed in the presence of a base, thereby forming an oxirane ring on the more sterically hindered side of the compound (9).

The compound (10) thus obtained is, for example, a mimic of sex pheromone of American cockroach, and can be converted into (+)-cis-pinocarveol (11) or (+)-neoisopinocampheol (12), useful as a trapping agent for the cockroach.

According to the above-described preparing methods 1) and 2), to which the present invention is applied, the target compounds (8) and (10) can be easily obtained as compared to the conventional methods [1) E. J. Corey and R. Noyori, Tetrahedron Lett., 311 (1970); 2) C. Nishino and H. Takayanagi, Agric. Biol. Chem., 43, 2399 (1979)], and therefore these preparing methods can be simple synthesizing methods of preparing intermediates useful for biologically active substance.

As described, with the epoxide preparing method of the present invention, easily synthesized can be an epoxide having an oxirane ring on the more sterically hindered side in the molecule, which is difficult to obtain with the conventional synthesizing methods.

The third object of the present invention, a method of preparing 1,6:3,4-dianhydro-β-D-talopyranose (1c), will now be described.

The method of preparing 1,6:3,4-dianhydro-β-D-talopyranose 1c) according to the present invention, includes two steps, (a') and (b'), and is characterized by use of the compound (2c) as a starting material.

In other words, the compound (1c) can be obtained by applying the steps (a) and (b) to the compound (2c).

Step (a'): the compound (2c) is reacted iodine to form an iodonium ion intermediate (4c) on the double bond position, and the intermediate is attacked by an acyloxy ion, thereby forming a 1,2-trans addact (3c).

Step (a')

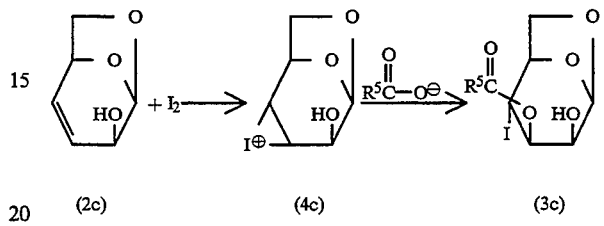

where $R^5$ is the same as defined above.

Step (b'): the 1,2-trans addact (3c) is hydrolyzed, and an oxirane ring is formed by the intramolecular nucleophilic substitution reaction with the elimination of an iodide ion, thereby obtaining a target compound (1c).

Step (b')

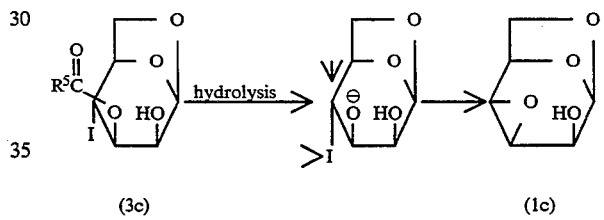

where $R^5$ is the same as defined above.

The present invention will now be described in detail.
1,6-anhydro-3,4-dideoxy-β-D-threo-hex-3-enopyranose (2c), which serves as a starting material, can be prepared by the methods disclosed in Japanese Patent Applications Nos. 2-272186, 3-77380, and 3-162604. In short, levoglucosenone (13) is reduced by a reducing agent, and the carbonyl group at the second position is reduced to an hydroxyl group having β orientation.

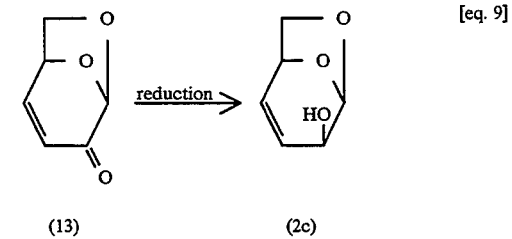

The reducing agent used in the reduction reaction is not particularly restricated, if a carbonyl group can be reduced to an alcohol thereby. For example, general reducing agents such as lithium aluminum hydride and sodium borohydride are preferably used.

The solvent used for the reaction should be selected in accordance with the reducing agent actually used, and ether etc is a preferable example.

The reaction condition is not particularly restricted, but generally, the reaction is carried out in a range of 0° C. and room temperature, and for a time period of 1 hour to 24 hours.

In the step (a'), the step of obtaining 1,2-adduct (3c) by addition of iodine and an acyloxy group to the compound (2c), can be conducted in a similar manner to the step (a) by the reaction of compound (2c) with iodine in the presence of the carboxylic acid (5) and the metal carboxylate (6). More specifically, one or more equivalent of iodine, and one or more equivalent of the carboxylic acid (5) or the metal carboxylate (6) for the double bond of the compound (2c) are mixed with the compound (2c) and stirred in an appropriate solvent.

The solvent of this reaction may be arbitrary except for water, alcohols, or those which release water or alcohols by hydrolysis. The solvent actually used in the step (a) can be used. It is preferable also in this reaction, that the carboxylic acid (5) itself be used as a solvent. In the case of using carboxylic acid (5), the carboxylic acid may be of arbitrary type as long as it is in a liquid state under the reaction condition, but acetic acid, propionic acid, and butyric acid are preferable, with acetic acid being most preferable.

The metal carboxylate (6) used in this reaction is not restricted, if it is the compound which can assiste to generate an iodonium ion from iodine. The metal carboxylate (6) is not essential to the reaction when a carboxylic acid is added to the reaction (including the case a carboxylic acid is used as the solvent), but if the metal carboxylate is added, the yield of product can be improved.

The reaction temperature and time period should be appropriately set, and in general, the temperature may be from room temperature to 50° C., and the time may be from 5 hours to 10 days.

The 1,2-trans addact (3c) obtained in this step can be used in the next step without being isolated.

The step (b') involves a reaction in which the acyloxy group of the 1,2-trans addact (3c) obtained in the step (a') is treated in the presence of a base, and the generated oxygen anion causes an intramolecular nucleophilic attack to the carbon atom at the fourth position with elimination of the iodide ion from the adduct, thereby forming an oxirane ring.

The base which can be used in this reaction is not restricted as long as a general acyloxy group can be hydrolyzed thereby. For example, the same base as listed in connection with the step (b) can be used.

The solvent which can be used in this reaction is not particularly restricted as long as it is generally used in hydrolysis. For example, methanol, ethanol, and water, which are preferably used in the step (b), are preferable.

The reaction temperature and time period should be appropriately set, and in general, the temperature may be from 0° C. to room temperature, and the time may be from 1 hour to 24 hours.

The stereochemistry of the above step will now be described in detail.

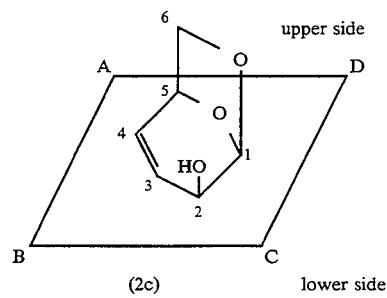

(2c)

In the compound (2c), the $C_1$—O—$C_6$ bond and OH at $C_2$ position are located on the same side (upper side) of the plane of the 6-membered ring, and only one side (upper side) of the plane of the 6-membered ring is sterically hindered. In this reaction, the compound (2c) is reacted with iodine in the presence of the carboxylic acid (5) or the metal carboxylate (6) to form an iodonium ion intermediate (4c). At this step, an iodonium ion approaches from the less hindered side of the 6-membered ring, i.e. the lower side of the ring. Thus, the iodonium ion as shown in compound (4c) is formed on the lower side of the ring. Since the lower side of the 6-membered ring is blocked by the iodonium ion in the intermediate (4c), an acyloxy ion attacks the carbon atom at the 3-position from the more hindered side (upper side) of the ring, thereby forming a 1,2-trans addact (3c). In this manner, iodine is introduced to the 4-position of the lower side of the ring which has less steric hindrance, whereas an acyloxy group is introduced to the 3-position of the upper side of the ring which has much steric hindrance.

The oxygen anion generated by the hydrolysis causes an intramolecular nucleophilic substitution reaction to form an oxirane ring. Since the oxygen anion is located on the upper side of the 6-membered ring, the oxirane ring is formed on the upper side of the ring, i.e. the more sterically hindered side as illustrated by [eq. 10] below.

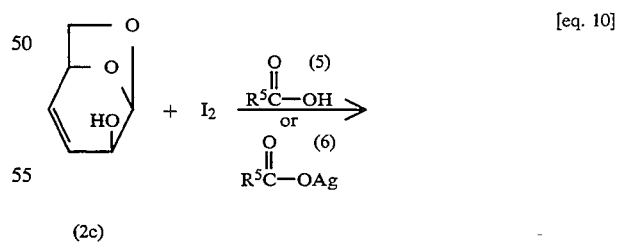

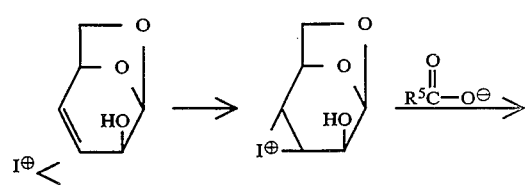

[eq. 10]

-continued

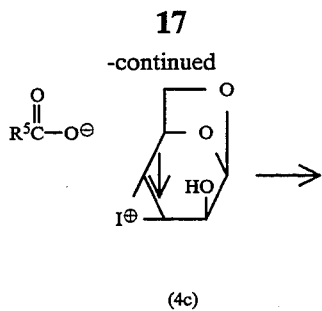

(4c)

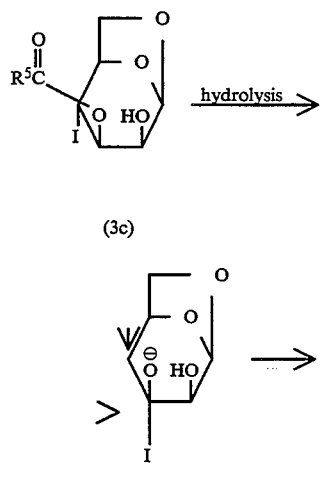

(3c)

(1c)

where $R^5$ is the same as defined above.

As described, with the method of the present invention, the target compound (1c) can be easily obtained from a widely available material (2c) at a high yield.

Further, the method of the present invention can be applied to not only general olefins, but also cyclic olefins without any drawbacks.

THE BEST EMBODIMENTS OF CARRYING OUT THE INVENTION

Figure 1A:
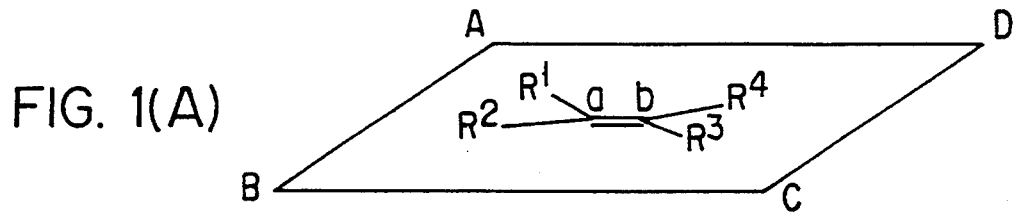
FIGS. 1(A)–(D) illustrate the stereochemistry in the step (a)
Figure 1B:
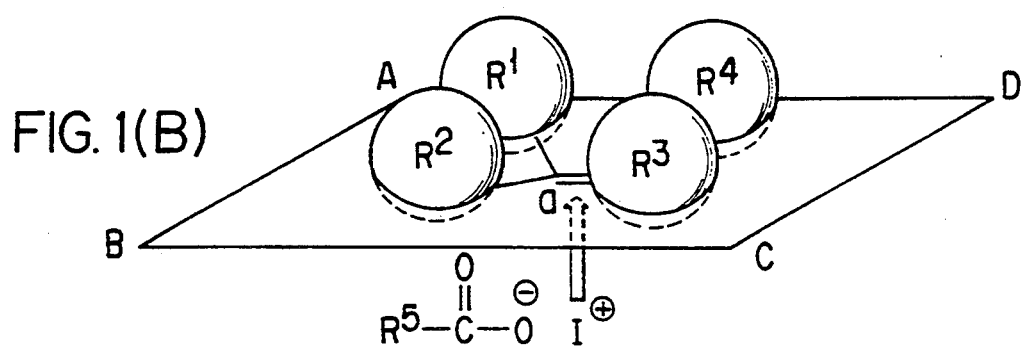
Figure 1C:
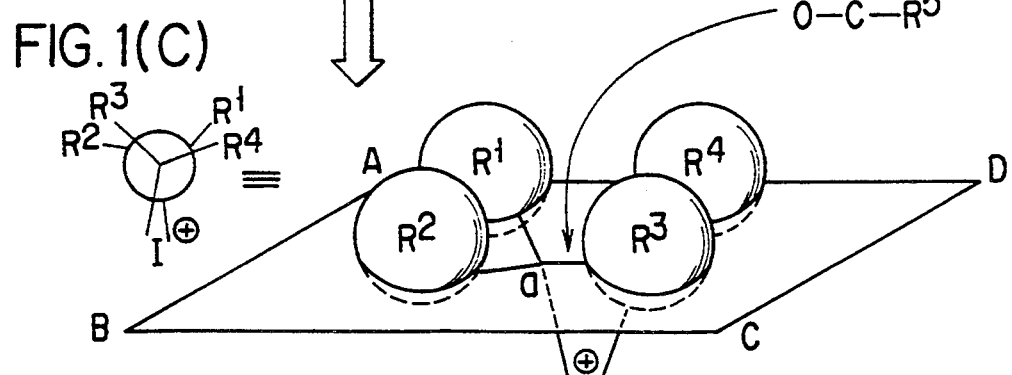
Figure 1D:
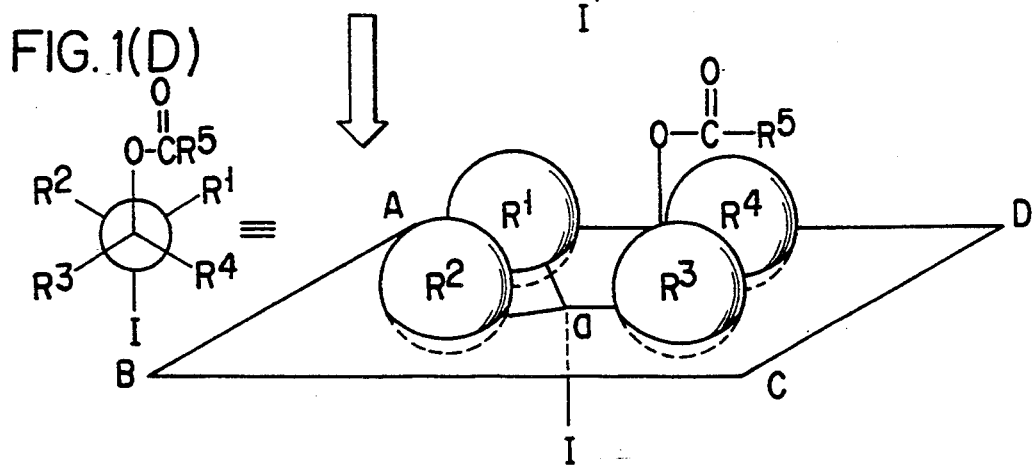
Figure 2A:
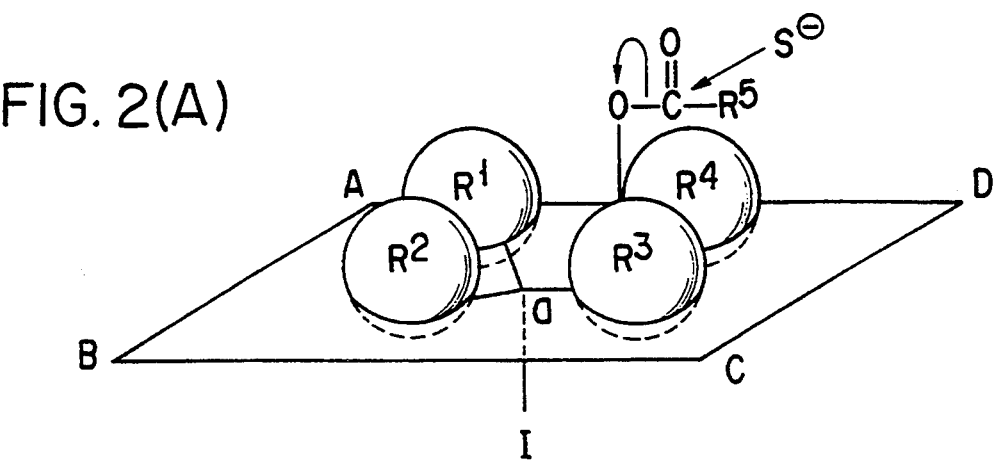
FIGS. 2(A)–(C) illustrate the stereochemistry in the step (b).
Figure 2B:
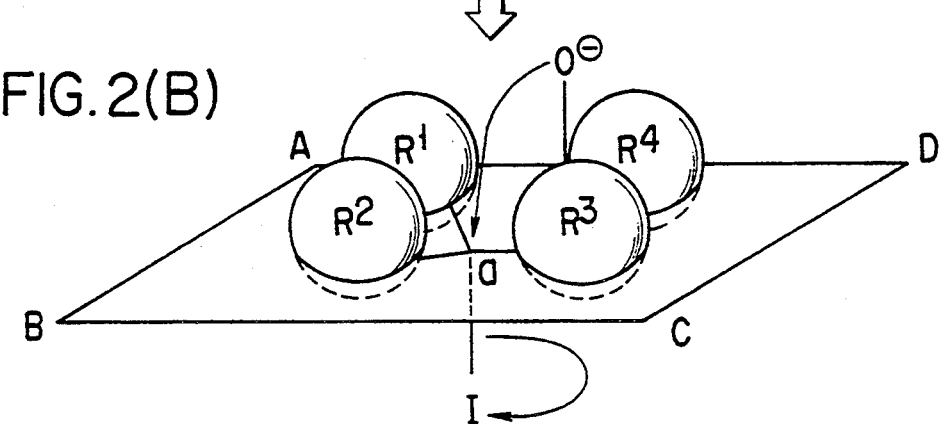
Figure 2C:
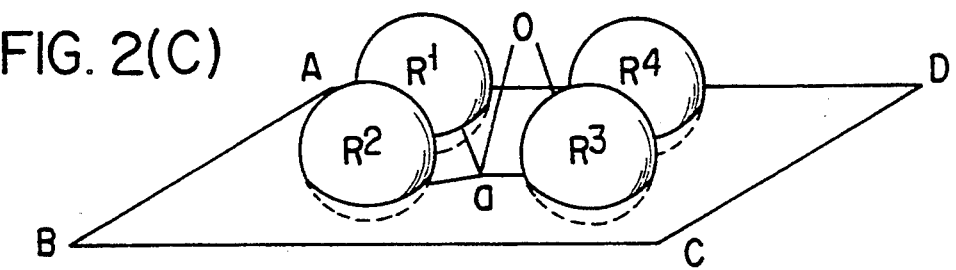

The present invention will now be described in detail with reference to examples.

EXAMPLES 1

Preparation of 1,6-anhydro-3,4-dideoxy-β-D-threo-hex-3-enopyranose (2c)

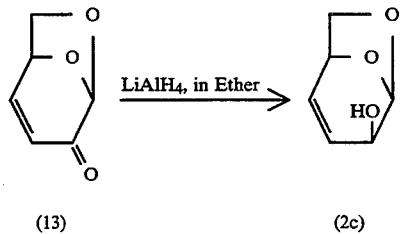

(13)　　　　　　　　(2c)

2.42 g (63.8 mmol) of lithium aluminum hydride was suspended in 200 ml of dry ether. 130 ml of dry ether in which 7.98 g (63.3 mmol) of levoglucosenone was dissolved was added dropwise to the suspension solution in a nitrogen atmosphere under ice-cooling. After the addition, the reaction mixture was stirred for one hour, and 4.60 g (256 mmol) of water was added dropwise. Then, methanol was added to the reaction mixture, and the undissolved substances were filtered off. The filtrate was concentrated under reduced pressure. The residue was purified by means of silica gel column chromatography (hexane: diethyl ether=1:1–1:2). The product was recrystallized from hexane-diethyl ether mixed solvent (hexane: diethylether=4:1), thereby obtaining 5.70 g of the target product (2c) (yield: 70.3%).

Melting Point: 65.6°–66.4° C.
$[a]^{25}_D$ —30.3° (c 1.00, CHCl$_3$)
IR $\nu_{max}$ (cm$^{-1}$) 3412 (br), 3050 (w), 1425 (m), 1259 (m), 1180 (m), 1125 (s), 1071 (s), 1046 (s)
$^1$H-NMR (CDCl$_3$ ppm from, TMS) 2.10 (1H, d, J=12.0 Hz; OH) 3.74–3.78 (1H, dd, J=4.1, 6.6 Hz; H-6) 3.84 (1H, d, J=6.6 Hz; H-6′) 4.34 (1H, m; H-2) 4.67 (1H, dd, J=4.1, 4.2 Hz; H-5) 5.52 (1H, b; H-1) 5.72 (1H, ddd, J=2.2, 2.2, 9.9 Hz; H-3) 6.12 (1H, dd, J=4.2, 9.9 Hz; H-4)

EXAMPLE 2

Synthesis of 1,6:3,4-dianhydro-β-D-talopyranose (1c)

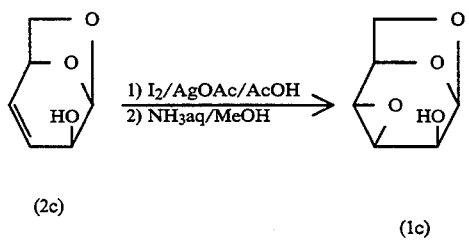

(2c)　　　　　　　　(1c)

0.13 g (1.00 mmol) of the compound (2c) was dissolved into 4.6 ml of acetic acid, and further 0.33 g (2.00 mmol) of silver acetate was added. While vigorously stirring the solution at room temperature, 0.27 g (1.05 mmol) of iodine was gradually added to the solution. After the solution was stirred for 5 hours at room temperature under nitrogen atmosphere, 40 ml of 25% ammonia water was gradually added to the solution under ice-cooling to make up to a basic solution. Further, 40 ml of methanol was added to the basic solution, and the solution was stirred for over night at room temperature. The undissolved substances were filtered off, and the filtrate was concentrated under reduced pressure. The residue was purified by means of silica gel column chromatography (hexane: ethyl acetate=1:1), thereby obtaining 1.09 g (yield: 93.8%) of the target product (1c). The target product was recrystallized from a hexane-diethyl ether mixed solvent (hexane:-diethyl ether=1:4).

The obtained product was confirmed to have the stereochenistry of the compound (1c) by x-ray structure analysis. Further, the values of the melting point, the angle of rotation, $^1$H-NMR spectrum, and $^{13}$C-NMR spectrum are identical to those listed in the literatures (A. E. Knauf, R. M. Hann and C. S. Hudson, J. Am. Chem. soc., 64, 925 (1942), T. Trnka, and M. Cerny, Carbohydr. Res., 76, 39 (1979)).

Melting Point: 74.0°–75.2° C.
$[a]^{24}_D$ —49.7° (c 1.44, H$_2$O)
$^1$H-NMR (CDCl$_3$, ppm from TMS) 2.41 (1H, d, J=12.2 Hz; OH) 3.34 (1H, ddd, J=1.0, 3.9, 3.9 Hz; H-3) 3.56 (1H, dd, J=4.7, 6.6 Hz; H-6) 3.83–3.76 (2H, m; H-2 and H-4) 3.95 (1H, d, J=6.6 Hz; H-6') 4.82 (1H, dd, J=4.7, 4.7 Hz; H-5) 5.30 (1H, d, J=3.8 Hz; H-1)

13C-NMR (CDCl3, ppm from CDCl3 (77.4 ppm) 98.2, 72.1, 68.9, 64.3, 57.6, 50.6

EXAMPLE 3

Synthesis of 1,6:3,4-dianhydro-β-D-talopyranose (1c)

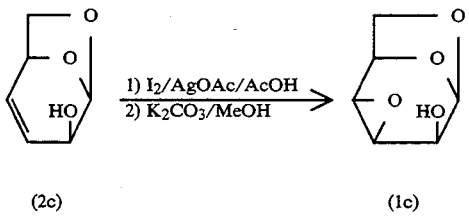

0.13 g (1.00 mmol) of the compound (2c) was dissolved into 4.6 ml of acetic acid, and further 0.33 g (2.00 mmol) of silver acetate was added. While vigorously stirring the solution at room temperature, 0.27 g (1.05 mmol) of iodine was gradually added to the solution. After the solution was stirred for 5 hours at room temperature under a nitrogen atmosphere, 150 ml of methanol, 10 ml of water, 7.7 g of potassium carboxylate, and 7.1 g of sodium hydrogencarbonate were gradually added to the solution under ice-cooling to make up to a basic solution. Further, the solution was stirred for over night at room temperature. The undissolved substances were filtered off, and the filtrate was concentrated under reduced pressure. The residue was purified by means of silica gel column chromatography (hexane: ethyl acetate=1:1), thereby obtaining 0.11 g (yield: 75.6%) of the target product (1c).

EXAMPLE 4

Synthesis of 1,6:3,4-dianhydro-β-D-talopyranose (1c)

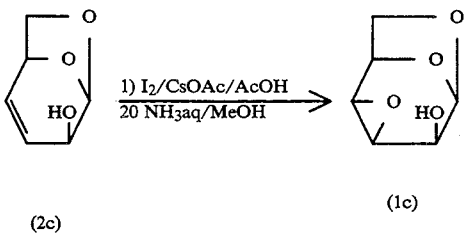

0.13 g (1.00 mmol) of the compound (2c) was dissolved into 4.6 ml of acetic acid, and further 0.96 g (5.00 mmol) of cesium acetate was added. While vigorously stirring the solution at room temperature, 0.80 g (1.05 mmol) of iodine was gradually added to the solution. After the solution was stirred for 5 hours at room temperature under nitrogen atmosphere, 40 ml of 25% ammonia water was gradually added to the solution under ice-cooling to make up to a basic solution. Further, 40 ml of methanol was added to the basic solution, and the solution was stirred for over night at room temperature. The undissolved substances were filtered off, and the filtrate was concentrated under reduced pressure. The residue was a mixture of the target product (1c) and the starting material (2c) in a ratio of 32:68 which was determined by 13C-NMR spectrum.

EXAMPLE 5

Synthesis of 1,6:3,4-dianhydro-β-D-talopyranose (1c)

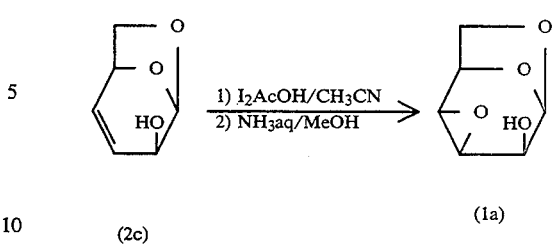

0.13 g (1.00 mmol) of the compound (2c) was dissolved into 7.0 ml of acetonitrile, and further 1.82 ml (31.8 mmol) of acetic acid was added. While vigorously stirring the solution at room temperature, 1.32 g (5.18 mmol) of iodine was gradually added to the solution. After the solution was stirred for 7 days at room temperature under nitrogen atmosphere, and then for 29 hours at 40° C., 40 ml of 25% ammonia water was gradually added to the solution under ice-cooling to make up to a basic solution. Further, 40 ml of methanol was added to the basic solution, and the solution was stirred for over night at room temperature. The undissolved substances were filtered off, and the filtrate was concentrated under reduced pressure. The residue was purified by means of silica gel column chromatography (hexane: ethyl acetate=1:1), thereby obtaining 0.05 g (yield: 31.9%) of the target product (1c).

As described, according to the method of the present invention, the material (1c), which is useful starting material for synthesis, can be obtained from levoglucosenone (13) at a overall yield of 66%. Conventionally, the compound (1c) is obtained by thermolysis of an endosperm of an ivory palm through a D-mannosane derivative in 5 steps, at yield of about 5%. With the method of the present invention, the compound (1c) can be obtained easily from a widely available material at a high yield, and therefore the method is believed to be more advantageous than the conventional ones.

Further, with the epoxide preparing method of the present invention, the drawback of the conventional method can be solved, and more specifically, it is possible to form an oxirane ring stereoselectively on the more sterically hindered side of an olefin at a high yield.

Industrial Applicability

With the epoxide preparing method of the present invention, it is possible to form an oxirane ring stereoselectively on the more sterically hindered side of an olefin at a high yield. Further, the preparing method involves a fewer reaction steps, and is easily operable, and therefore the method can be applied to the large scale synthesis of the target product.

In the case of synthesizing prostaglandine, which is useful as an anti-inflammatory agent or a medicine for diseases of the circulatory system, the method of the present invention can be applied to 2-oxabicyclo[3.3.-0]oct-6-en-3-one as a starting materials to give an epoxide having a desired configuration (cis-syn-cis). The method of the present invention can be applied also to a synthesizing method of terpenes having a pinane skeleton. More specifically, with the method of the present invention, α-pinene can be more easily transformed into (+)-cis-pinocarveol (11) or (+)-neoisopinocampheol (12), which is useful as a sex pheromone trapping agent of American cockroach, than with the conventional methods. AS described, there are many synthesizing methods in connection with epoxides, which can be improved by the method of the present invention.

We claim:

1. A method of preparing an epoxide represented by formula 1a) or (1b):

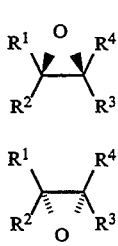

(1a)

(1b)

wherein $R^1$, $R^2$, $R^3$ and $R^4$ represent a hydrogen atom or a straight or branched chain alkyl group, and $R^1$ and $R^4$ and/or $R^2$ and $R^3$ may be bonded with each other to form rings,
comprising the steps of
(a) reacting an olefin represented by formula (2)

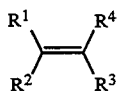

(2)

wherein $R^1$, $R^2$, $R^3$ and $R^4$ are the same as defined above, and the olefin represented by formula (2) exists as one of two isomers and each isomer has a structure in which one side of the plane constituted by the double bond, $R^1$, $R^2$, $R^3$ and $R^4$ is more sterically hindered in comparison with the other side,
with iodine in the presence of an acyloxy ion generating compound; and
(b) treating the reaction mixture obtained in step (a) in the presence of a base, thereby forming an oxirane ring stereoselectively on the more sterically hindered side of the olefin.

2. A method of preparing an epoxide from an olefin represented by formula (2)

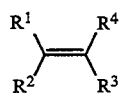

(2)

wherein $R^1$, $R^2$, $R^3$ and $R^4$ represent a hydrogen atom or a straight or branched chain alkyl group, and $R^1$ and $R^4$ and/or $R^2$ and $R^3$ may be bonded with each other to form rings, and the olefin represented by formula (2) exists as one of two isomers and each isomer has a structure in which one side of the plane constituted by the double bond, $R^1$, $R^2$, $R^3$ and $R^4$ is more sterically hindered in comparison with the other side,
comprising the steps of
(a) obtaining a 1,2-trans adduct represented by formula (3a) or (3b) having an acyloxy group on the more sterically hindered side of the double bond by reacting said olefin represented by formula (2) with iodine in the presence of an acyloxy ion generating compound as follows

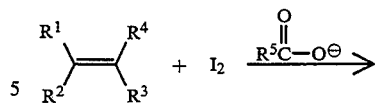

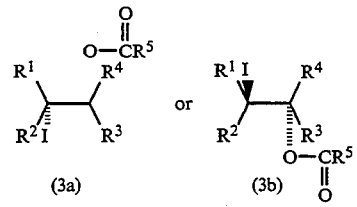

(3a) (3b)

wherein $R^1$, $R^2$, $R^3$ and $R^4$ are the same as defined above and $R^5$ represents an alkyl group or an aryl group; and
(b) forming an oxirane ring on the more sterically hindered side of the olefin by hydrolyzing the 1,2-trans adduct represented by formula (3a) or (3b) and eliminating an iodide ion as follows

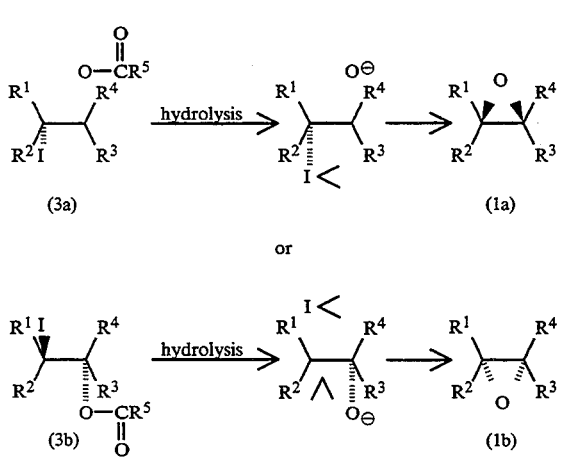

wherein $R^1$, $R^2$, $R^3$, $R^4$ and $R^5$ are the same as defined above.

3. The method of preparing an epoxide according to claim 1 or 6, wherein a ring is formed between $R^1$ and $R^4$ and/or $R^2$ and $R^3$ in the olefin represented by formula (2).

4. The method of preparing an epoxide according to claims 1 or 2, wherein the olefin represented by formula (2) is 1,6-anhydro-3,4-dideoxy-β-D-threo-hex-3-enopyranose represented by formula (2c)

(2c)

5. The method of preparing an epoxide according to claim 1 or 6, wherein the olefin represented by formula (2) is selected from the group consisting of α-pinene, β-pinene and 2-oxabicyclo[3,3,0]oct-6-en-3-one.

6. The method of preparing an epoxide according to claim 1, wherein the base in step (b) is selected from the group consisting of an alkali metal hydroxide, an alkali metal carbonate, a metal alkoxide and aqueous ammonia.

7. The method of preparing an epoxide according to claim 1, wherein the base in step (b) is selected from the group consisting of sodium hydroxide, potassium hydroxide, sodium carbonate, potassium carbonate, sodium methoxide, potassium butoxide and aqueous ammonia.

8. The method of preparing an epoxide according to claim 1 or 2, wherein the acyloxy ion generating compound is a carboxylic acid represented by formula (5) or a metal carboxylate represented by formula (6)

(5)

(6)

wherein $R^5$ represents an aryl or alkyl group and M represents a metal selected from the group consisting of silver or cesium.

9. The method of preparing an epoxide according to claim 1, wherein the acyloxy ion generating compound is selected from the group consisting of silver acetate, silver benzoate and cesium acetate.

10. The method of preparing an epoxide according to claim 1 or 2, wherein step (a) is carried out in the presence of a solvent selected from the group consisting of carboxylic acid, hexane and acetonitrile.

11. The method of preparing an epoxide according to claim 1, wherein step (a) is carried out in the presence of a solvent selected from the group consisting of acetic acid, formic acid, propionic acid and butyric acid.

12. The method of preparing an epoxide according to claim 1 or 1, wherein step (b) is carried out in the presence of a solvent selected from the group consisting of methanol, ethanol and water.

13. A method of preparing 1,6:3,4-dianhydro-β-D-talopyranose represented by formula (1c)

(1c)

comprising the steps of
(a) reacting 1,6-anhydro-3,4-dideoxy-β-D-threo-hex-3-enopyranose represented by formula (2c)

(2c)

with iodine in the presence of an acyloxy ion generating compound represented by the formula

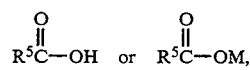

wherein $R^5$ represents an aryl or alkyl group and M represents a metal selected from the group consisting of silver or cesium, to form an iodonium ion intermediate represented by formula (4c) that is attached by an acyloxy ion of the acyloxy ion generating compound, to thereby obtain a 1,2-trans adduct represented by formula (3c) as follows

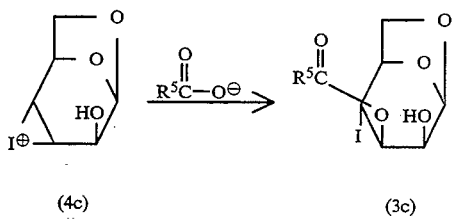

(4c)          (3c)

and
(b) hydrolyzing the 1,2-trans adduct represented by formula (3c) with a base selected from the group consisting of an alkali metal hydroxide, an alkali metal carbonate, a metal alkoxide and aqueous ammonia, to thereby cause the elimination of an iodide ion to obtain the 1,6:3,4-dianhydro-β-D-talopyranose represented by formula (1c).

14. The method of preparing an epoxide according to claim 13, wherein the base in step (b) is selected from the group consisting of sodium hydroxide, potassium hydroxide, sodium carbonate, potassium carbonate, sodium methoxide, potassium butoxide and aqueous ammonia.

* * * * *